United States Patent [19]

Geysen

[11] Patent Number: 4,833,092

[45] Date of Patent: May 23, 1989

[54] METHOD FOR DETERMINING MIMOTOPES

[75] Inventor: Hendrik M. Geysen, Knoxfield, Australia

[73] Assignee: Commonwealth Serum Laboratories Commission, Victoria, Australia

[21] Appl. No.: 10,088

[22] PCT Filed: Apr. 22, 1986

[86] PCT No.: PCT/AU86/00110

§ 371 Date: Dec. 22, 1986

§ 102(e) Date: Dec. 22, 1986

[87] PCT Pub. No.: WO86/06487

PCT Pub. Date: Nov. 6, 1986

[30] Foreign Application Priority Data

Apr. 22, 1985 [AU] Australia ............... PH0240

[51] Int. Cl.[4] .................. G01N 33/53; G01N 33/543; G01N 33/577

[52] U.S. Cl. .................. 436/501; 436/518; 436/543; 436/548

[58] Field of Search ............... 436/518, 543, 548, 501

[56] References Cited

U.S. PATENT DOCUMENTS 4,554,101 11/1985 Hopp ..................... 424/85

FOREIGN PATENT DOCUMENTS

| 25428 | 9/1984 | Australia . |
| 36563 | 6/1985 | Australia . |
| 36562 | 6/1985 | Australia . |
| 36560 | 6/1985 | Australia . |
| 45339 | 1/1986 | Australia . |
| WO84/02983 | 8/1984 | PCT Int'l Appl. . |
| WO84/03564 | 9/1984 | PCT Int'l Appl. . |
| WO85/02121 | 5/1985 | PCT Int'l Appl. . |

OTHER PUBLICATIONS

Hopp, Thomas P. et al., Proc. Natl. Acad. Sci., U.S.A., 78(6), 3824–3828 (Jun. 1981).
Geysen, H. Mario et al., Molecular Immunology, 23(7), 709–715 (1986).
Scientific American, Feb. 1983, pp. 48–56, (p. 50, lines 33–39), R. A. Lerner, "Synthetic Vaccines".

*Primary Examiner*—Sidney Marantz
*Attorney, Agent, or Firm*—Sughrue, Mion, Zinn, Macpeak & Seas

[57] ABSTRACT

A method of detecting or determining the sequence of monomers which is a topographical equivalent of the ligand which is complementary to a particular receptor of interest, the method comprising the steps of:

1. synthesizing a plurality of catamers, each said catamer being of the general formula:

$$D_2 - D_1$$

wherein $D_1$ represents a designated monomer selected from a first set of monomers, and $D_2$ represents a designated monomer selected from a second set of monomers which may be the same as or different to said first set of monomers; said plurality of catamers comprising catamers in which each designated monomer is systematically varied to contain members from the respective set of monomers;

2. contacting each catamer with the receptor of interest, and, 3. detecting or determining the presence or absence of binding between each catamer and said receptor.

36 Claims, No Drawings

METHOD FOR DETERMINING MIMOTOPES

This invention relates to a method of detecting or determining a sequence of monomer molecules which corresponds to the ligand molecule for a particular receptor. The sequence of monomer molecules so determined is the mimotope (defined below) of the particular ligand. The mimotope which is determined by this method may not have any obvious or direct relationship to the natural ligand molecule, but will share with it the ability to react with the receptor, and indeed, the mimotope so determined may be modified to incorporate specific or additional properties in the reaction with the receptor. Such a mimotope could then be used to replace the natural ligand in the treatment or prevention of particular disease or it may be used to mediate a particular biological effect.

As used throughout this specification, the terms listed below have the following meanings:

receptor: a molecule or molecular complex which will combine specifically with its particular ligand molecule. It is those receptors which on binding with their particular ligand(s) mediate a biological function that are of most interest. Examples of receptors include, but are not restricted to, the common class of receptors associated with the surface membrane of cells and include, for instance, the immunologically important receptors of B-cells, T-cells, macrophages and the like. Another example is receptors for acetyl choline on nerve cells which cause a nerve pulse to be transmitted down the length of the neuron when the receptor molecule reacts with its ligand, acetyl choline.

epitope: the specific surface of an antigen molecule which is delineated by the area of interaction with the sub-class of receptors known as antibodies.

catamer: a polymer molecule which is a precisely defined linear sequence formed by the condensation of small molecules. Note that this term includes molecules in which different types of condensation reactions are used to join the small molecules. A number prefixed to the word "catamer" implies that the catamer is formed by the condensation of the indicated number of small molecules, for example, 8-catamer means that the catamer is made up from eight small molecules. Examples of catamers include any given peptide and any given oligo-saccharide.

monomer: a member of the set of small molecules which can be condensed together to form a catamer. The set of monomers includes but is not restricted to, for example, the set of common L-amino acids, the set of D-amino acids, the set of synthetic amino acids, the set of nucleotides, and the set of pentoses and hexoses.

peptide: a catamer in which the small molecules are alpha-amino acids and which are joined together through a peptide bond. In the context of this specification it should be appreciated that the amino acids may be the L-optical isomer or the D-optical isomer.

mimotope: a catamer which in at least one of its conformations has a surface region with the equivalent molecular topology to the binding surface of the ligand molecule of which it is the mimic. In the context of immunological receptors, the mimotope mimics the epitope of the antigen.

complementary: refers to the matching together of the reacting surfaces of an ligand molecule and its receptor. Thus, the receptor and its ligand can be described as complementary, and furthermore, the contact surface characteristics are complementary to each other.

paratope: the combining site of an antibody which is complementary to a particular epitope.

ligand molecule: is the molecule which binds to a particular receptor and when bound to it mediates the biological function associated with that particular receptor.

Examples of receptors which can be investigated by this method include, but are not restricted to:

hormone receptors: for instance the receptors for insulin and Growth Hormone; determination of the mimotopes of the ligands binding to these receptors may lead to the development of an oral replacement of the daily injections which diabetics must take to relieve the symptoms of diabetes, and in the other case, a replacement for the scarce human Growth Hormone which can only be obtained from cadavers or by recombinant DNA technology. Other examples are the vaso-constrictive hormone receptors; determination of the mimotope of the ligand binding to these receptors may lead to the development of drugs to control blood pressure.

opiate receptors: determination of mimotopes of the ligands binding to the opiate-receptors in the brain may lead to the development of less-addictive replacements for morphine and related drugs.

microorganism receptors: determination of mimotopes of the ligands binding to a receptor such as specific transport proteins or enzymes essential to survival to microorganisms, may lead to a new class of antibiotics. Of particular value would be antibiotics against protozoa and those bacteria resistant to the antibiotics in current use.

enzymes: for instance, the enzymes responsible for cleaving neural transmitters; determination of mimotopes able to modulate the action of the enzymes which cleave the different neural transmitters may lead to the development of drugs which can be used in the treatment of disorders of neural transmission; and, antibodies: for instance the ligand-binding site on the antibody molecule which combines with the epitope of an antigen of interest; determination of a mimotope for the epitope may lead to the development of vaccines of which the immunogen is based on one or more mimotopes or diagnostic agents or compounds useful in the therapeutic treatment of autoimmune diseases.

Examples of ligands which can be investigated by this method include, but are not restricted to:

toxins and venoms: for instance, the combining site of the toxin molecule which reacts with a particular receptor in the body to give the particular symptom(s) of intoxication; determination of mimotopes to the combining site of the ligand may lead to the development of drugs which can be used to treat envenomation by snakes and other poisonous animals without the side effects of heterologous antivenenes.

virus and other microorganism capsid molecules: for instance, the combining site on the virus coat molecule which reacts with a particular receptor on the cell membrane in the body and which allows the virus to invade and thus infect the particular cell; determination of mimotopes to this combining site may lead to the development of drugs which specifically prevent intracellular invasion by the virus and thus prevent their replication.

It is a primary object of this invention to detect or determine one or more short sequences of monomers (catamers) which selectively combine with a particular receptor so as to mediate its biological function. These catamers are the mimotopes of the ligand. This information is invaluable for the design of very specific diagnostic and therapeutic agents.

The most usual group of small molecules which may be condensed together to form a catamer is the group of alpha-amino acids. However, other molecules which are consistent with a different chosen chemistry may also be used; for example, catamers formed from the specified sequential condensation of nucleotides or saccharides. Another group of small molecules would be the non-genetically coded amino acids such as beta-amino acids, which may be used to advantage to add an additional bond at specified positions within the catamer.

The method of the present invention is based on the realisation that a given receptor will specifically react with a catamer which is the mimotope for the ligand to which the receptor is directed. It further relies on modern techniques of immunology to detect reaction between a receptor and its ligand when both are present.

In Australian Patent Specification No. 45339/85 it is proposed to delineate mimotopes based on an overall length of about 8 monomers. It is now clear that the preferred method for the delineation of mimotopes is from shorter catamers (2 or 3 monomers long) made up from all combinations of monomers from either:

(i) two sets of monomers, which may be identical; or
(ii) three sets of monomers, of which the centre monomer of the catamer is selected from a set of special chosen monomers which confer known spatial relationships on the other two monomers, the remaining monomers of the catamer coming from two sets of monomers which may be identical.

Furthermore, it has now been shown that the sensitivity of detection of binding to receptors is reduced in some instances where the monomers are synthesized in cafamer preparations as disclosed in Patent Specification No. 45339/85.

We have now demonstrated that reaction is readily detected between a receptor and short mimotopes. These short mimotopes when condensed together then bind to the receptor with either a greater affinity or with greater specificity for that receptor. This reaction can be detected even when the short mimotope presented to the receptor is as small as two monomer molecules long. By determining the optimum short mimotope at each stage and then testing further variants, the final structure of a strongly-binding mimotope can be determined.

According to the present invention there is provided a method of detecting or determining the sequence of monomers which is a topographical equivalent of the ligand which is complementary to the particular receptor of interest and prior knowledge is irrelevant about the identity, structure and sequence of the receptor or its ligand. The method comprises the steps of:

1. synthesizing a plurality of catamers, each said catamer being of the general formula:

$D_2$—$D_1$

wherein $D_1$ represents a designated monomer selected from a first set of monomers, and $D_2$ represents a designated monomer selected from a second set of monomers which may be the same as or different to said first set of monomers; said plurality of catamers comprising catamers in which each designated monomer is systematically varied to contain members from the respective set of monomers;

2. contacting each catamer with the receptor of interest, and, 3. detecting or determining the presence or absence of binding between each catamer and said receptor.

The method may also comprise the further steps of:

a. synthesizing a further plurality of catamers, each said catamer being of the general formula:

$D_3$—$D_2$—$D_1$,

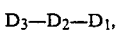

or $D_2$—$D_1$—$D_3$

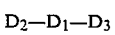

wherein $D_1$ and $D_2$ are as defined above, and preferably represent a combination of monomers corresponding to a catamer which binds to said receptor, and $D_3$ represents a designated monomer selected from a third set of monomers which may be the same as or different to either the first or the second set of monomers, and b. performing steps 2 and 3 as described with the further plurality of catamers.

The procedure of steps a. and b. above may be repeated to further "extend" the catamers by systematically adding further monomers to the catamers, and testing in the same manner as in step b, above.

In another important aspect, the method of this invention may comprise the steps of:

A. synthesizing a plurality of additional catamers, each said additional catamer being of the general formula:

$D_2$—Sp—$D_1$

wherein $D_1$ and $D_2$ are as defined above and Sp is a spacer molecule which can modify the relative orientation of the monomers $D_1$ and $D_2$; and B. performing steps 2 and 3 as described above with the plurality of additional catamers.

The spacer molecule "Sp" as described above may also be systematically introduced into all possible positions of the "extended" catamers referred to above, and tested in the same manner as in Step B. above.

In yet another aspect, the method of the invention may further comprise the steps of systematically replacing the monomers in any of the catamers referred to above with their optical isomers, either individually or in combinations of monomers, and again performing steps 2 and 3 as described above.

In a further aspect, the method may further comprise the steps of systematically replacing the monomers in any of the catamers referred to above which bind with the receptor of interest, either individually or in combinations of monomers, with other monomers selected from the respective set(s) of monomers, and again performing steps 2 and 3 as described above.

It will be apparent that the method of this invention requires no previous information about the nature of the ligand and in particular it requires no foreknowledge of the sequence of monomers which make up the ligand. In fact, it is not necessary for the application of this invention to know the source or identity of the ligand to which the receptor is directed. Furthermore, this invention makes no assumptions about the nature of the ligand of the particular receptor. This method will identify mimotopes of discontinuous as well as continuous ligands. Because of the very nature of the method of the invention it will be appreciated that mimotopes may or may not consist of members of the same set of monomers which make up the ligand of which it is the mimic.

The plurality of catamers required to be synthesized in the application of this invention may be prepared by any of the known method of catamer synthesis. The preferred methods when the monomers are amino acids is to use the solid phase technique described in Australian Patent Specification No. 25429/84, whereby each catamer is synthesized on a polyethylene support.

The following is a detailed description of one embodiment of the present invention when applied to the determination of a mimotope for a ligand able to bind to a receptor when that receptor is an antibody. In this context, the ligand is usually referred to as the epitope for the antibody. Preferably the method of the present invention is carried out by screening a plurality of synthesized catamers against the antibody of interest. Ideally the antibody will be a monoclonal antibody which can be prepared by any of the usual methods. Polyclonal antiserum from humans and animals may be used if a source of monoclonal antibody with the desired characteristics is not available, however, analysis of the resulting data may be complicated because the reaction observed could be from more than one monoclonal antibody. When using polyclonal antiserum it may be necessary to reduce the antibody diversity by using techniques well known to those skilled in the art, for example iso-electric focusing, HPLC-based chromatography or affinity chromatography.

Current indications suggest that an epitope mimicked by a catamer which is usually about six monomers in length when the monomers come from the set of alpha-amino acids. It is to be understood, however, that the present invention is not retricted to sequences formed from six monomers. The ability of the 6-catamer to be the mimotope of the epitope is not critically dependent on every position having a designated monomer. It has been found that certain positions in most mimotopes are not restricted to a single designated monomer for binding with the receptor.

A. Synthesis of a plurality of catamers.

As noted above, the preferred method of applying this invention is to synthesize the catamers on a solid support. In this embodiment, the plurality of catamers will all have the general formula:

$$Y—D_2—D_1—Lk—\text{(solid support)},$$

where "Lk" represents a linker molecule which provides a suitable end group for condensing the monomers to the solid support. "$D_1$" and "$D_2$" represent designated positions occupied by monomers which are selected from known sets of monomers; but which are altered systematically between catamers. It should be noted that the set of monomers used for the $D_1$ designated position need not be the same set of monomers used for the $D_2$ designated position. "Y" in the general formula is an end group of the catamer and may be, but is not restricted to, for example a hydrogen atom or an acetyl group. "Y" may also be another molecule which is coupled to the catamer to preserve particular characteristics of the molecular environment of a peptide bond at the amino terminal designated position.

If i is the number of members in the set of monomers to be coupled in the $D_1$ position and j is the number of members in the set of monomers to be coupled in the $D_2$ position then a total of i.j different catamers will be synthesized.

In the present embodiment, the support rods are prepared so that the monomers can be coupled to them by coupling an appropriate linker molecule.

For the coupling at the $D_1$ position, each rod will be treated with a reaction mixture which contains only a single monomer such as a protected amino acid or the like. In this position each of the i monomers are coupled to j rods. For the coupling at the $D_2$ position each rod is treated with a reaction mixture which contains a single monomer such as a protected amino acid or the like. Each of the j rods which has a particular monomer in the $D_1$ position will have a different monomer coupled at the $D_2$ position. In this way every combination of the members of the set(s) of monomers will be found in the i.j rods.

The desired end group, "Y", is then coupled using the appropriate chemistry.

After synthesis of the plurality of catamers any side-chain protective groups are removed from the catamers using the appropriate techniques and the rod-coupled catamers are washed.

It has been found to be a preferred embodiment of the invention to synthesize more than one set of plurality of catamers to aid in the analysis of data. Thus, as well as synthesizing catamers with the general formula $$Y—D_2—D_1—Lk—\text{(solid support)}$$

as described above, additional sets of catamers may be prepared with the general formula $$Y—D_2—Sp—D_1—Lk—\text{(solid support)}$$

where "Sp" is a spacer molecule which may restrict the relative orientation of the monomers at the designated positions to a particular geometrical configuration(s). The spacer molecule may also be deliberately chosen to allow a greater flexibility to the relative geometric configuration between monomers in the designated positions, $D_1$ and $D_2$. It should be noted that members of the set of spacer molecules may be made up from the condensation of more than one monomer. Examples of spacer molecules include, but are not restricted to glycine (approximately linear extension), beta-alanine (increased flexibility), proline (forced bend), glycyl-proline (extended bend, otherwise known as reverse bend in protein structure terminology) and o-aminobenzoic acid (a planar bend).

By analyzing the results from these sets of catamers the preferred spatial relationships between monomers in the mimotopes can be deduced as will be shown in the appropriate examples given below.

B. Testing of the plurality of catamers.

The plurality of catamers prepared as in A. above are then contacted with the particular antibody of interest. The reaction between antibody and each catamer can then be detected by any of the usual methods, for example, radioimmunoassay (RIA). However, the preferred method of detection is to use the well known enzyme-linked immunosorbent assay (ELISA).

At the end of each assay antibodies can be removed from the catamers by, for example, washing with a solution of 8M urea, 0.1% 2-mercaptoethanol and 0.1% sodium dodecylsulphate followed by several washes in phosphate buffered saline. In this way the plurality of catamers may be used for testing with many other antibodies.

C. Analyses of the data

In the testing of a set of catamers with antibody it has been found that certain catamers will show detectable binding with the antibody. These reacting catamers identify useful combinations of the members of the set(s) of monomers. These combinations of monomers are short mimotopes which, when extended, may bind to the antibody with a greater affinity or alters specificity. Analysis of the data is greatly facilitated by including a number of control peptides in the synthesis which aid the determination of significant responses. Further analysis of the data can be carried out in a number of ways. These include:

1. permutating each of these reacting combinations of monomers to create a list of catamers which will include mimotopes which bind to the paratope; each catamer in this list can be regarded as a possible mimotope;

2. selecting candidates from the list of reacting combinations of monomers and further synthesizing sets of catamers in which the known reacting combination of monomers is held constant and further monomers are added systematically at either end; thus in the example above, a suitable set of such catamers would include catamers with the formulae $$Y—D_3—A_2—A_1—Lk—(solid\ support]$$

and $$Y—A_2—A_1—D_3—Lk—(solid\ support]$$

where $A_1$ and $A_2$ constitute the reacting combination of monomers from the previous results and $D_3$ is the new designated position where each of the members of the set of monomers is systematically varied; and 3. combining the results from different sets of a plurality of catamers and analyzing the results to deduce a single sequence of monomers, or a small number of such sequences which would bind to the antibody of interest. Analysis of this data is possible as the reacting combinations of monomers when they are adjacent to each other are now known, as well as the reacting combinations of monomers when they have particular geometrical configurations between them. In this way, these data can then be interpreted to predict the structure of the mimotope when bound to the antibody; this approach will be of greatest benefit when the antibody used to test the plurality of catamers is a monoclonal antibody.

The procedure given in 2. above can be repeated until no further enhancement of binding is achieved by additional extending of the mimotope. Ideally, the sequence of the mimotope should be checked by regularly synthesizing and testing replacement nets of the mimotope to obtain the optimally-binding mimotope for further extension as described in Australian Patent Specification No. 25428/84.

D. Synthesis of selected catamers

The selected catamers can be synthesized using similar methods to those used in A. After the selected catamers have been synthesized they are reacted with the antibody of interest. It is then simple to select the catamer which binds most strongly with the antibody.

The binding of the mimotope with the antibody can be further enhanced by synthesizing a further plurality of catamers based on the sequence of the most strongly binding mimotope. This plurality of catamers consists of adding spacer molecules (—Sp—) systematically at all positions of the mimotope; and where feasible systematically replacing each monomer of the catamer with its optical isomer. Testing of this set of catamers with the antibody will give invaluable information about the relative orientation of the monomers and their stereochemistry as required for binding with the antibody.

In Examples 1, 2, 3 and 4 given below, the mimotopes are being determined for the antigen against which different monoclonal antibodies were raised. The defined set of monomers is the set of the common L-alpha acids unless otherwise specified. The linker molecule, —Lk—, was 3 amino-$N^1$(6-aminohexyl)-propanamide and the end group, Y—, was the acetyl moiety. In Example 5 below, the mimotope is determined for an antigenic determinant of human chorionic gonadotrophin which induced a monoclonal antibody. The linker molecule, —Lk—, is the same as that used in earlier Examples. The end group, Y—, is either β-alanyl-β-alanine or β-alanine. The defined set of monomers was extended to include the D-optical isomers of the common alpha amino acids and several unusual amino acids. In Example 6 below, the mimotope is determined for a receptor site on viruses. The linker molecule, —Lk—, is the same as for earlier Examples. The end group, Y—, is either β-alanyl-β-alanine or β-alanine. The defined set of monomers was extended as described for Example 5.

EXAMPLE 1

A monoclonal antibody was raised against sperm whale myoglobin using the usual techniques. This monoclonal antibody was tested against a set of catamers with the general formula:

$$Y—D_2—D_1—Lk—(solid\ support].$$

Three pairs of reacting monomers bound to the catamers with approximately equal response and were significantly higher than other pairs of monomers. The sequences were E-F, E-L and E-H.

A further set of catamers was synthesized which comprised all 4-catamers which could be made from the set of monomers; Glutamic acid (E), Phenylalanine (F), Histidine (H) and Leucine (L). The following catamers were found to bind significantly higher than the remaining catamers:

L—H—E—F

L—H—F—E

F—L—H—E

F—H—L—E

H—H—F—L

This small group of short mimotopes can now become the candidates for further extensions.

EXAMPLE 2

A monoclonal antibody was raised against sperm whale myoglobin using the usual techniques. This monoclonal antibody was tested against a set of catamers with the general formula:

$$Y—D_2—D_1—Lk—(solid\ support].$$

Three pairs of reacting monomers bound to the catamers with approximately equal response and were significantly higher than other pairs of monomers. The sequences were E-F, E-L and E-H.

Six further sets of catamers were synthesized using the pairs E-F, E-L and E-H as starting points. Using the E-F pair as an example, the catamers in each set had the general formula:

Y—E—F—Lk—(solid support), or

Y—E—Sp—F—Lk—(solid support), where Sp is a spacer molecule from the set of beta-alanine, glycine and L-proline. Furthermore the D-optical isomer of both the Glutamic acid and Phenylalanine were systematically substituted for the L-optical isomer.

The catamers which gave the best response from each set of catamers were D-Glutamic acid—L-Proline—L-Phenylalanine L-Glutamic acid—L-Leucine, and D-Glutamic acid—L-Proline—D-Histidine. These results show that the monomers F and H were better positioned non-adjacent to E; furthermore, E and L are best positioned adjacent. The optical isomers in the catamers which gave the best binding suggest a structure for a strongly binding mimotope as set out below. It is to be noted that the sperm whale myoglobin molecule does have a region which is similar to the predicted mimotope. Obviously, this predicted mimotope becomes a candidate for further extension.

The structure below is a two dimensional representation of the spatial relationship between the amino acids, F, E, L, and H when bound to a monoclonal antibody against sperm whale myoglobin (see Example 2). It must be noted that this is an illustration only and must not be interpreted to mean that the catamer illustrated is planar. Furthermore, the bonds joining F to E and L to H are meant to represent a distance greater than that of a peptide bond.

```
   F
   |
   E - L
       |
       H
```

When this structure is compared with the X-ray crystallography structure of myoglobin, it is of considerable interest to note that the sequence —F—L—E—L— appears at positions 135 to 138 and that there are two histidine residues (at positions 81 and 82) in close proximity to the glutamic acid at position 136. This gives considerable credence to the postulated structure of the epitope of the monoclonal antibody.

EXAMPLE 3

A mimotope to a monoclonal antiserum raised against Foot and Mouth Disease Virus was delineated to the sequence W—Q—M—G—H—S. A series of catamers were synthesized in which a beta-alanine residue was introduced systematically between monomers. The sequence W—Q—M—$\beta$—G—H—S gave a response which was significantly larger than the base sequence, where $\beta$ represents beta-alanine. It was further found that excellent binding to the antibody was achieved with the sequences:

W—Q—M—$\beta$—$\beta$—H—S

W—Q—M$\beta$—$\beta$—$\beta$—H—S which suggests that the glycine in the starting mimotope was a spacer between two reacting elements, W—Q—M and H—S. Thus it can be clearly seen that the mimotope is made up of two parts; furthermore, the joining together of these parts is not critical for the mimotope to be able to react strongly with the antibody.

A further set of catamers were synthesized in which the D-optical isomer systematically replaced the L-optical isomer monomer in the starting mimotope. The results of testing with the antibody showed that for strongest binding, the monomers in each element should have the same optical isomer and that there was a preference for the monomers in the W—Q—M element to be the D-optical isomers whereas the monomers in element H—S should be L-optical isomers. These results can be interpreted to mean that the epitope to the antibody is made up of two adjacent anti-parallel chains in which the chain direction is M—Q—W and the second chain is H—S. This prediction leads to the suggestion that another mimotope to the monoclonal antibody would be:

G—H—S—$\beta$—G—W—Q—M

This was synthesized and found to react with comparable binding to the antibody as the strongly binding catamer:

W—Q—M—$\beta$—G—H—S.

Thus, the way in which the two elements W—Q—M and H—S are joined together is irrelevant to the ability to combine with the antibody so long as their relative positions remain the same. The best mimotope as a potential immunogen will be one in which these elements are joined together from both sides in order to minimize conformational mobility.

EXAMPLE 4

A monoclonal antibody (SO93-7) raised against Foot and Mouth Disease virus was tested with catamers with the general formula:

Y—$D_2$—$D_1$—Lk—(solid support]

It was found that the dipeptide Q-F reacted significantly more strongly with the monoclonal antibody than with any other dipeptide.

Further sets of catamers were synthesized with the general formulae:

Y—Q—F—$D_3$—Lk—(solid support]

and

Y—$D_3$Q—F—Lk—(solid support]

When these sets of catamers were reacted with the antiserum it was found that the following catamers reacted significantly better with the monoclonal antibody than any of the others:

H—Q—F

N—Q—F

G—Q—F

Q—F—Q

Q—F—G

This small group of short mimotopes can now become the candidates for further extensions.

EXAMPLE 5

A monoclonal antibody (S218-4) was raised against human chorionic gonadotrophin using the usual techniques. This was tested with catamers with the general formula:

$Y_1$—$D_2$—$D_1$—Lk—(solid support)

where $Y_1$— is β-alanyl-β-alanine. It was found that the dipeptide in the designated positions which bound most strongly to the monoclonal antibody was F-A.

Further sets of catamers were synthesized with the general formulae:

$Y_2$—$D_3$—Sp—F—A—Lk—(solid support)

and $Y_1$—F—A—Sp—$D_3$—Lk—(solid support)

where Sp is a spacer which is an element of the set [null, β-alanine], and $Y_2$— is the end group, β-alanyl. The set of monomers used in the designated position $D_3$ was extended to include both the L— and D— optical isomers of the common alpha amino acids, and the unusual amino acids, α-amino butyric acid, γ-amino butyric acid, L-norcleucine, sarcosine, ornithine, L-norvaline, L-homophenylalanine, β-alanine. When these sets of catamers were reacted with the monoclonal antibody it was found that the catamers which reacted strongly were:

$Y_2$—$P_D$—F—A and $Y_2$—$A_D$—F—A where $P_D$ and $A_D$ represent the D-optical isomers of proline and alanine, respectively.

Further sets of catamers were synthesized with the general formulae:

$Y_2$—$D_4$—Sp—$P_D$—F—A—Lk—(solid support)

$Y_1$—$P_D$—F—A—Sp—$D_4$—Lk—(solid support)

and $Y_2$—$D_4$—Sp—$A_D$—F—A—Lk—(solid support)

and $Y_1$—$A_D$—F—A—Sp—$D_4$—Lk—(solid support)

where the extended set of monomers was used in the designated position $D_4$. When these sets of catamers were reacted with the monoclonal antibody it was found that the catamer which reacted most strongly was:

$Y_1$—$P_D$—F—A—$D_D$ where $D_D$ represents the D-optical isomer of aspartic acid.

Further sets of catamers were synthesized with the general formulae:

$Y_2$—$D_5$—Sp—$P_D$—F—A—$D_D$—Lk—(solid support)

and $Y_1$—$P_D$—F—A—$D_D$—Sp—$D_5$—Lk—(solid support)

where the extended set of monomers was used in the designated position $D_5$. When these sets of catamers were reacted with the monoclonal antibody it was found that the catamer which reacted most strongly with the antibody was:

$Y_2$—$R_D$—β—$P_D$—F—A—$D_D$ where β represents β-alanine and had been included in the synthesis of the catamer as a spacer.

Pretreatment of the monoclonal antibody with human chorionic gonadotrophin completely removed the ability of the antibody to react with the catamer β—$R_D$—β—$P_D$—F—A—$D_D$ thus illustrating the specificity of the mimotope.

EXAMPLE 6

This Example illustrates the application of the invention to the detection of a mimotope to a receptor which is not an antigen to which an antibody has been raised. This Example detects mimotopes of a receptor to which a virion binds. In this case the test system for detecting binding to catamers has to be modified. In this Example, the synthesized catamers are allowed to react with influenza virus particles (strain A-Shearwater/1/72). After reaction the catamers are washed to remove unbound virus particles. The presence of bound virus particles was detected by reacting with a polyclonal antibody (S227-1) which had been raised against the haemaglutinin of influenza virus A/Shearwater/1/72. Antibodies which had reacted with the bound virus were detected in the usual way by ELISA.

A set of catamers was synthesized with the general formula:

$Y_1$—$D_2$—$D_1$—Lk—(solid support)

where the end group, $Y_1$—, is β-alanyl-β-alanine. The set of monomers which was used in the designated positions $D_1$ and $D_2$ consisted of the D- and L- optical isomers of the common alpha amino acids. When the catamers were reacted with a suspension of influenza virions strain A/Shearwater/1/72, particles bound to dipeptides at the designated positions:

$A_D$—K $I_D$—K

N—$I_D$ and $$M_D—I_D$$

where the suffix "D" indicates the D-optical isomer of the indicated amino acid. After removal of the bound virus from the catamers, the catamers were reacted with the polyclonal antibody S227-1 at the same concentration as that used to detect bound virus to ensure that the peaks found were due to binding of virus rather than binding of the polyclonal antibody.

Further sets of catamers were synthesized with the general formulae:

$$Y_2—D_3—Sp—A_D—K—Lk—(solid\ support]$$

$$Y_1—A_D—K—Sp—D_3—Lk—(solid\ support]$$

where $Y_1$— represents the β-alanine end group and Sp is an element of the set of spacers, [null, β-alanine]. The set of monomers used at the designated position $D_3$ was the extended set as described in Example 5. When these sets of catamers were reacted with influenza virus strain A/Shearwater/1/72, virions bound most strongly to the catamer:

$$Y_1—A_D—K—K_D$$

This Example demonstrates that the invention can be applied to the determination of mimotopes of receptor molecules and ligands in general. Implementation of the method is limited only by the ability to detect the presence of binding to the set of catamers.

I claim:

1. A method of detecting or determining the sequence of monomers which is a topographical equivalent of the ligand which is complementary to a particular receptor of interest, the method comprising the steps of:
    1. synthesizing a plurality of catamers, each said catamer being of the general formula:

$$D_2—D_1$$

wherein $D_1$ represents a designated monomer selected from a first set of monomers, and $D_2$ represents a designated monomer selected from a second set of monomers which may be the same as or different from said first set of monomers; said plurality of catamers comprising catamers in which each designated monomer is systematically varied to contain members from the respective set of monomers;
    2. contacting each catamer with the receptor of interest, and,
    3. detecting or determining the presence or absence of binding between each catamer and said receptor.

2. A method according to claim 1, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

3. A method according to claim 1, wherein each of said plurality of catamers is synthesized on a solid support, and has the general formula:

$$Y—D_2—D_1—Lk—(solid\ support)$$

wherein $D_1$ represents a designated monomer selected from a first set of monomers, and $D_2$ represents a designated monomer selected from a second set of monomers which may be the same as or different from said first set of monomers, Lk represents a linker molecule, and Y is a end group of the catamer.

4. A method according to claim 1, comprising the further step of systematically replacing the monomers in any of the catamers with their optical isomers, either individually or in combinations of monomers, and again performing the following steps: contacting each catamer with the receptor of interest, and detecting or determining the presence or absence of binding between each catamer and said receptor.

5. A method according to claim 4, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

6. A method according to claim 1 comprising the further steps of:
    A. synthesizing a plurality of additional catamers, each said additional catamer being of the general formula:

$$D_2—Sp—D_1$$

wherein $D_1$ represents a designated monomer selected from a first set of monomers, and $D_2$ represents a designated monomer selected from a second set of monomers which may be the same as or different from said first set of monomers, and Sp is a spacer molecule which can modify the relative orientation of the monomers $D_1$ and $D_2$;
    B. contacting each said additional catamer with the receptor of interest, and,
    C. detecting or determining the presence or absence of binding between each said additional catamer and said receptor.

7. A method according to claim 6, wherein each of said plurality of additional catamers is synthesized on a solid support, and has the general formula:

$$Y—D_2—Sp—D_1—Lk—(solid\ support)$$

wherein $D_1$ represents a designated monomer selected from a first set of monomers, and $D_2$ represents a designated monomer selected from a second set of monomers which may be the same as or different from said first set of monomers, Sp is a spacer molecule which can modify the relative orientation of the monomers $D_1$ and $D_2$, Lk represents a linker molecule and Y is an end group of the catamer.

8. A method according to claim 6, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

9. A method according to claim 6, comprising the further step of systematically replacing the monomers in any of the catamers with their optical isomers, either individually or in combinations of monomers, and again performing the following steps: contacting each catamer with the receptor of interest, and detecting or determining the presence or absence of binding between each catamer and said receptor.

10. A method according to claim 9, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

11. A method according to claim 1, comprising the further steps of:
   a. synthesizing a further plurality of catamers, each said catamer being of the general formula:

$D_3—D_2—D_1$, or $D_2—D_1—D_3$ wherein $D_1$ represents a designated monomer selected from a first set of monomers, and $D_2$ represents a designated monomer selected from a second set of monomers which may be the same as or different from said first set of monomers, and $D_3$ represents a designated monomer selected from a third set of monomers which may be the same as or different from either the first or the second set of monomers, and
   b. contacting each said catamer with the receptor of interest, and,
   c. detecting or determining the presence or absence of binding between each said catamer and said receptor.

12. A method according to claim 11, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

13. A method according to claim 11, comprising the further step of systematically replacing the monomers in any of the catamers with their optical isomers, either individually or in combinations of monomers, and again performing the following steps: contacting each catamer with the receptor of interest, and detecting or determining the presence or absence of binding between each catamer and said receptor.

14. A method according to claim 13, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

15. A method according to claim 11, wherein steps a., b. and c. are repeated with the systematic introduction of a spacer molecule, Sp, which can modify the relative orientation of the monomers $D_1$ and $D_2$, into all possible positions of the further pluralities of the catamers.

16. A method according to claim 15, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

17. A method according to claim 15, comprising the further step of systematically replacing the monomers in any of the catamers with their optical isomers, either individually or in combinations of monomers, and again performing the following steps: contacting each catamer with the receptor of interest, and detecting or determining the presence or absence of binding between each catamer and said receptor.

18. A method according to claim 17, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

19. A method according to claim 11 comprising the further steps of:
   A. synthesizing a plurality of additional catamers, each said additional catamer being of the general formula:

$D_2—Sp—D_1$ wherein $D_1$ represents a designated monomer selected from a first set of monomers, and $D_2$ represents a designated monomer selected from a second set of monomers which may be the same as or different from said first set of monomers, and Sp is a spacer molecule which can modify the relative orientation of the monomers $D_1$ and $D_2$;
   B. contacting each said additional catamer with the receptor of interest, and,
   C. detecting or determining the presence or absence of binding between each said additional catamer and said receptor.

20. A method according to claim 19, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

21. A method according to claim 19, wherein each of said plurality of additional catamers is synthesized on a solid support, and has the general formula:

Y—D$_2$—Sp—D$_1$—Lk—(solid support)

wherein D$_1$ represents a designated monomer selected from a first set of monomers, and D$_2$ represents a designated monomer selected from a second set of monomers which may be the same as or different from said first set of monomers, Sp is a spacer molecule which can modify the relative orientation of the monomers D$_1$ and D$_2$, Lk represents a linker molecule and Y is an end group of the catamer.

22. A method according to claim 19, comprising the further step of systematically replacing the monomers in any of the catamers with their optical isomers, either individually or in combinations of monomers, and again performing the following steps: contacting each catamer with the receptor of interest, and detecting or determining the presence or absence of binding between each catamer and said receptor.

23. A method according to claim 22, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

24. A method according to claim 11, wherein steps a., b. and c. are repeated with the systematic addition of further monomers to the catamers.

25. A method according to claim 24, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

26. A method according to claim 24, comprising the further step of systematically replacing the monomers in any of the catamers with their optical isomers, either individually or in combinations of monomers, and again performing the following steps: contacting each catamer with the receptor of interest, and detecting or determining the presence or absence of binding between each catamer and said receptor.

27. A method according to claim 26, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

28. A method according to claim 24, wherein steps a., b. and c. are repeated with the systematic introduction of a spacer molecule, Sp, which can modify the relative orientation of the monomers D$_1$ and D$_2$, into all possible positions of the further pluralities of the catamers.

29. A method according to claim 28, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

30. A method according to claim 28, comprising the further step of systematically replacing the monomers in any of the catamers with their optical isomers, either individually or in combinations of monomers, and again performing the following steps: contacting each catamer with the receptor of interest, and detecting or determining the presence or absence of binding between each catamer and said receptor.

31. A method according to claim 30, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

32. A method according to claim 24 comprising the further steps of:
A. synthesizing a plurality of additional catamers, each said additional catamer being of the general formula:

D$_2$—Sp—D$_1$ wherein D$_1$ represents a designated monomer selected from a first set of monomers, and D$_2$ represents a designated monomer selected from a second set of monomers which may be the same as or different from said first set of monomers, and Sp is a spacer molecule which can modify the relative orientation of the monomers D$_1$ and D$_2$;
B. contacting each said additional catamer with the receptor of interest, and,
C. detecting or determining the presence or absence of binding between each said additional catamer and said receptor.

33. A method according to claim 32, comprising the further step of systematically replacing the monomers in any of the catamers which bind with the receptor of interest, either individually or in combinations of monomers, with other monomers selected from the respective set(s) of monomers, and again performing the following steps: contacting each catamer with the receptor of interest, and detecting or determining the presence or absence of binding between each catamer and said receptor.

34. A method according to claim 32, wherein each of said plurality of additional catamers is synthesized on a solid support, and has the general formula:

Y—D$_2$—Sp—D$_1$—Lk—(solid support)

wherein D$_1$ represents a designated monomer selected from a first set of monomers, and D$_2$ represents a designated monomer selected from a second set of monomers which may be the same as or different from said first set of monomers, Sp is a spacer molecule which can modify the relative orientation of the monomers $D_1$ and $D_2$, Lk represents a linker molecule and Y is an end group of the catamer.

35. A method according to claim 32, comprising the further step of systematically replacing the monomers in any of the catamers with their optical isomers, either individually or in combinations of monomers, and again performing the following steps: contacting each catamer with the receptor of interest, and detecting or determining the presence or absence of binding between each catamer and said receptor.

36. A method according to claim 35, comprising the further step of systematically replacing the monomers in any of the catamers which bind the receptor of interest, either individually or in combinations of monomers, with other monomers selected from the respective set(s) of monomers, and again performing the following steps: contacting each catamer with the receptor of interest, and detecting or determining the presence or absence of binding between eact catamer and said receptor.

* * * * *